United States Patent
Okazoe et al.

Patent Number: 5,856,337
Date of Patent: *Jan. 5, 1999

[54] 2-ARYLQUINOLINES AND PROCESS FOR PRODUCING THE SAME

[75] Inventors: Takashi Okazoe; Yoshitomi Morizawa, both of Kanagawa, Japan

[73] Assignees: Asahi Glass Co., Ltd., Tokyo; The Green Cross Corporation, Osaka, both of Japan

[*] Notice: This patent issued on a continued prosecution application filed under 37 CFR 1.53(d), and is subject to the twenty year patent term provisions of 35 U.S.C. 154(a)(2).

[21] Appl. No.: 788,013

[22] Filed: Jan. 24, 1997

[30] Foreign Application Priority Data

Jan. 25, 1996 [JP] Japan .................... 8-011257

[51] Int. Cl.$^6$ .................... C07D 215/18; A61K 31/47; A61K 31/475

[52] U.S. Cl. .................... 514/311; 514/314; 546/118; 546/173

[58] Field of Search .................... 546/118, 173; 514/311, 314

[56] References Cited

FOREIGN PATENT DOCUMENTS 0569013  11/1993  European Pat. Off. .
0812841  12/1997  European Pat. Off. .

OTHER PUBLICATIONS

Miyadera et al., "Studies on Quinolizinium Salts–VI[1] the Reaction of Quinolizinium Ion with Aniline[2]", Tetrahedron 25:837–845 (1969).
Phillips et al., 'Quino[1,2-c]Quinazolines. I. Synthesis of Quino[1,2-c]Quinazolinium. . . ., J. Heter. Chem., 17:1489–1495 (1980).
Elderfield et al., "Synthesis of 2–Phenyl–4–Chloroquinolines", J. Am. Chem. Soc. 68:1272–1276 (1946).
Database Crossfire, Beilstein Informationssysteme GbmH; Frankfurt, DE; XP–002060234, (1997).
Database Crossfire, Beilstein Informationssysteme GmbH; Frankfurt, DE; XP–002020235 (1997).
Database Crossfire, Beilstein Informationssyteme GmbH; Frankfurt, DE; XP–002060236 (1997).
Database Crossfire, Beilstein Informationssysteme GmbH; Frankfurt, DE; XP–002020237 (1997).
Chemical Abstracts 110:8105, Reddy, abstract of Indian J Chem, Sect B, 1988, 27B(6), pp. 563–564.
Chemical Abstracts 110:135063, Atwell, abstract of J Med Chem, 1989, 32(2), pp. 396–401.
Chemical Abstracts 105:60452, Shaikah, abstract of J Med Chem, 1986, 29(8), pp. 1329–1340.
Chemical Abstracts 94:121454, Phillips, abstracts of J Heterocycl Chem, 1980, vol. 17(7), pp. 1489–1495.
Chemical Abstracts 86:29597, Lown, abstract of Dep Chem, Can J Chem, 1976, vol. 54(16), pp. 2563–2572.
Chemical Abstracts 70:96591, Miyadera, abstract of Tetrahedron, 1969, vol. 25(4), pp. 837–845.
Chemical Abstracts 106:119710, Atwell, abstract of EP 206802, Dec. 1986.
Chemical Abstracts 75:76768, Sheinkman, abstract of SU 301334, Feb. 1971.
Chemical Abstracts 74:76298, Sheinkman, abstract of Dopov Akad Nauk Ukr RSR, Ser. B, 1970, vol. 32(7), pp. 619–623.
Chemical Abstracts 100:6508, Haviv, abstract of US Patent #4407803, Oct. 1983.
Chemical Abstracts 96:162509, Chorbadzhiev, abstract of God Sofii Univ, Khim Fak 1981, vol. date 1977, 72, Pt 1, pp. 147–150.
Chemical Abstracts 87:167845, Hamana, abstract of Chem Pharm Bull, 1977, vol. 25(6), pp. 1256–1264.
Chemical Abstracts 84:134888, Badr, abstract of Can J Chem, 1975, vol. 53(24), pp. 3831–3836.
Chemical Abstracts 73:130926, Hamana, abstract of Fac Pharm Sci, Kyushu Univ, Fukuoka, Japan, Yakugaku Zasshi, 1970, 90(8), 991–1000.

*Primary Examiner*—Alan L. Rotman
*Assistant Examiner*—D. Margaret Mach
*Attorney, Agent, or Firm*—Sughrue, Mion, Zinn, Macpeak & Seas, PLLC

[57] ABSTRACT

2-Arylquinolines represented by formula (1):

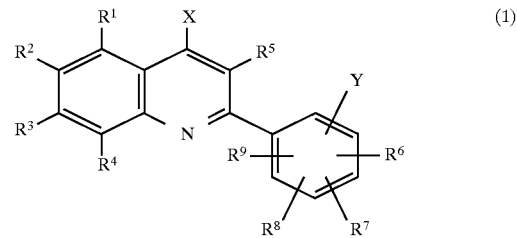

wherein $R^1$, $R^3$ to $R^9$ each represents hydrogen, halogen, lower alkyl, cyclic lower alkyl, aryl, aralkyl, alkoxy or $-C_mF_{2m+1}$; $R^2$ represents hydrogen, halogen, lower alkyl, cyclic lower alkyl, aryl, aralkyl, alkoxy, $-C_nF_{2n+1}$ or $-CH_2Q$, in which Q represents a monovalent organic group obtained by eliminating from an organic compound having $-NH-$ the hydrogen atom bonded to the nitrogen, or halogen; X represents halogen or hydrogen; Y represents nitro or amino which may be protected with a protecting group; and m and n each represents an integer of from 1 to 6; and processes for producing the 2-arylquinolines.

29 Claims, No Drawings

2-ARYLQUINOLINES AND PROCESS FOR PRODUCING THE SAME

FIELD OF THE INVENTION

The present invention relates to 2-arylquinolines, which are useful as intermediates in producing quinoline compounds useful as a remedy for hypertension. Also, the present invention relates to processes for producing the 2-arylquinolines.

BACKGROUND OF THE INVENTION

Blood pressure of a living organism is regulated by the sympathetic nervous system, the balance between the pressor system and the depressor system, and the like. The renin-angiotensin system participates in the pressor system. Renin would act on angiotensinogen to produce angiotensin I. Then, angiotensin I is converted into angiotensin II by an angiotensin I converting enzyme. Angiotensin II is a potent vasoconstrictor, acting on the adrenal cortex to promote the secretion of aldosterone, thus causing an increase in the blood pressure. Angiotensin II exerts its function via an angiotensin II receptor on the cell membrane. Therefore, an antagonist to angiotensin II is usable as a remedy for hypertension caused by angiotensin II, similar to an angiotensin I converting enzyme inhibitor.

Although peptidergic angiotensin II antagonists such as saralasin are known, these antagonists show reduced effectiveness in orally administration because of their peptidergic nature. On the other hand non-peptidergic angiotensin II antagonists have been reported (e.g., JP-A-56-71074, JP-W-3-501020, WO 9319060, and the like; the terms "JP-A" and "JP-W" as used herein mean an "unexamined published Japanese patent application" and an "unexamined published Japanese international patent application", respectively) and are efficacious when administered orally. Recently, it has been proposed to use quinoline compounds having a 2-arylquinoline skeleton as non-peptidergic angiotensin II antagonists (JP-A-5-230022, JP-A-5-239053, JP-A-6-16659, JP-A-6-80664, and the like).

Of the quinoline compounds as described above, the compounds disclosed in JP-A-6-80664 have particularly excellent properties as angiotensin II antagonists. Of the compounds, N-{2-{6-[(2-ethyl-5,7-dimethyl-3H-imidazo[4, 5-]pyridin-3-yl)methyl]quinolin-2-yl}phenyl}trifluoromethanesulfonamide and salts thereof are expected to be highly useful as a remedy for hypertension because these compounds are very readily absorbed in vivo. The present invention provides intermediates in the synthesis of these quinoline compounds having a trifluoromethanesulfonamido group and a process for producing these intermediates.

SUMMARY OF THE INVENTION

An object of the present invention is to provide intermediates of quinoline compounds having a 2-arylquinoline skeleton which are useful as angiotensin II antagonists and a process for producing the same. In particular, an object of the present invention is to provide intermediates which are useful in synthesizing quinoline compounds containing a trifluoromethanesulfonamido group (—NHSO$_2$CF$_3$) at the 2-position of the phenyl group and a process for producing these intermediates. A preferred group of the quinoline compounds having a trifluoromethanesulfonamido group (—NHSO$_2$CF$_3$) at the 2-position of the phenyl group is the compounds having a (3H-imidazo[4,5-b]pyridin-3-yl) methyl group at the 6-position of the quinoline skeleton, with the proviso that the 3H-imidazo[4,5-b]pyridine ring preferably has a substituent(s) such as an alkyl group and the like. Among these, N-{2-{6-[(2-ethyl-5,7-dimethyl-3H-imidazo[4,5-b]pyridin-3-yl)methyl]quinolin-2-yl}phenyl}trifluoromethanesulfonamide is preferred.

These and other objects of the present invention have been attained by providing a 2-arylquinoline represented by the following formula (1) and processes for preparing it as set forth below.

A 4-halo-2-(nitrophenyl)quinoline represented by formula (1), wherein X represents a halogen atom and Y represents a nitro group, is prepared by a process which comprises reacting a 2-(nitrophenyl)-4-quinolone represented by the following formula (2), wherein Y represents a nitro group, with a halogenation agent.

A (quinolin-2-yl)aniline represented by formula (1), wherein X represents a hydrogen atom and Y represents an amino group, is prepared by a process which comprises reducing the above-mentioned 4-halo-2-(nitrophenyl) quinoline with a reducing agent in the presence of a base.

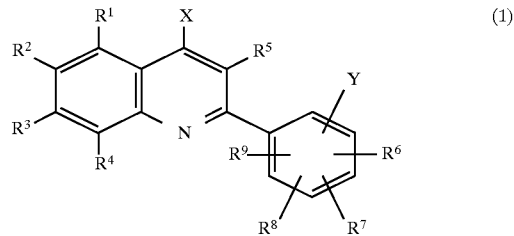

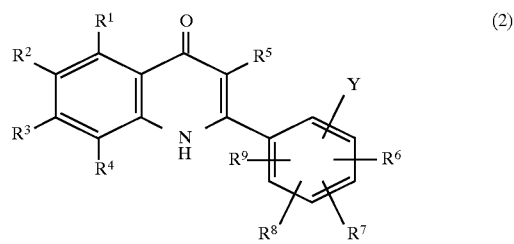

In formulae (1) and (2),

R$^1$, R$^3$, R$^4$, R$^5$, R$^6$, R$^7$, R$^8$ and R$^9$ each independently represents a hydrogen atom, a halogen atom, a lower alkyl group, a cyclic lower alkyl group, an aryl group, an aralkyl group, an alkoxy group or —C$_m$F$_{2m+1}$;

R$^2$ represents a hydrogen atom, a halogen atom, a lower alkyl group, a cyclic lower alkyl group, an aryl group, an aralkyl group, an alkoxy group, —C$_n$F$_{2n+1}$ or —CH$_2$Q, in which Q represents a monovalent organic group obtained by eliminating from an organic compound having an —NH— group the hydrogen atom bonded to the nitrogen atom or Q represents a halogen atom; and m and n each independently represents an integer of from 1 to 6.

Also, in formula (1), X represents a halogen atom or a hydrogen atom; and Y represents a nitro group, an amino group or an amino group protected with a protecting group. In formula (2), Y represents a nitro group.

DETAILED DESCRIPTION OF THE INVENTION

The term "lower" in the organic groups of the present invention as used herein means that the organic groups have from 1 to 6 carbon atoms.

Examples of the "lower alkyl group" include a methyl group, an ethyl group, a propyl group, an isopropyl group, a butyl group, an isobutyl group, a t-butyl group, a pentyl group and a hexyl group.

The "halogen atom" includes a fluorine atom, a chlorine atom, a bromine atom and an iodine atom.

The "alkoxy group" is preferably a lower alkoxy group, and more preferably an alkoxy group having not more than 4 carbon atoms. Examples thereof include a methoxy group, an ethoxy group, a propoxy group and a butoxy group.

The "cyclic lower alkyl group" is a cycloalkyl group containing a ring having from 3 to 6 carbon atoms. Examples thereof include a cyclopropyl group, a cyclobutyl group, a cyclopentyl group and a cyclohexyl group.

The "aryl group" is a monovalent aromatic hydrocarbon group and preferably a phenyl group and derivatives thereof. Examples thereof include a phenyl group, a tolyl group and a p-halophenyl group.

The "aralkyl group" is an alkyl group substituted with an aryl group, and the alkyl group preferably has not more than 4 carbon atoms. Examples thereof include a benzyl group, a benzhydryl group, a trityl group and a phenethyl group.

The above aryl group and the aryl group in the above aralkyl group may be substituted with at least one substituent, and the substituent is preferably a lower alkyl group or a halogen atom.

The amino group protected with a protecting group for use in the present invention includes amino groups protected with a protecting group which has been known and used as a protecting group for an amino group. Examples of the protecting group include an acyl group, an alkoxycarbonyl group, an alkyl group, an alkenyl group, an aralkyl group, a triorganosilyl group and a sulfonyl group. Preferred examples of the acyl group include an acetyl group, a benzoyl group and a trifluoroacetyl group. Preferred examples of the alkoxycarbonyl group include a t-butoxycarbonyl group and a benzyloxycarbonyl group. Preferred examples of the alkyl, alkenyl and aralkyl groups include a methyl group, an ethyl group, an allyl group, a benzyl group, and a trityl group. Preferred examples of the triorganosilyl group include a t-butyldimethylsilyl group, a t-butyldiphenylsilyl group, a triethylsilyl group and a triphenylsilyl groups. Examples of the sulfonyl group include a p-toluenesulfonyl group, a benzenesulfonyl group, a p-chlorobenzenesulfonyl group and a methanesulfonyl group.

Q represents a monovalent organic group obtained by eliminating from an organic compound having an —NH— group the hydrogen atom bonded to the nitrogen atom, or a halogen atom. The organic compound having an —NH— group is preferably a heterocyclic compound wherein the nitrogen atom in the —NH— group is a ring constituent. The heterocyclic compound may be a fused heterocyclic ring compound. The organic compound having an —NH— group may be an aliphatic amine compound, an alicyclic amine compound or an aromatic amine compound, each having at least a primary or secondary amino group. The halogen atom represented by Q is preferably a bromine atom or a chlorine atom, and more preferably a bromine atom.

Preferred Q other than a halogen atom is a substituted heterocyclic compound as those described in JP-A-6-16659 and JP-A-6-80664 as described above. Of those, Q is more preferably a 1H-imidazol-1-yl group having a substituent(s) and represented by, for example, the following formula (3), or a 3H-imidazo[4,5-b]pyridin-3-yl group represented by, for example, the following formula (4), and most preferably a 2-ethyl-5,7-dimethyl-3H-imidazo[4,5-b]pyridin-3-yl group:

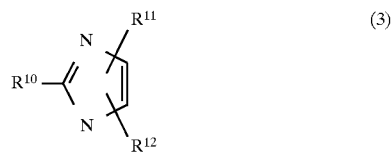

(3)

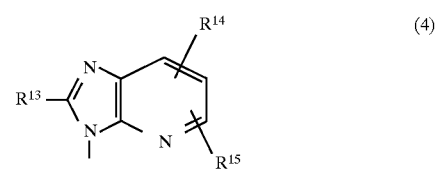

(4)

In formulae (3) and (4), $R^{10}$ to $R^{15}$ are defined below.

$R^{10}$ and $R^{13}$ each independently represents a lower alkyl group, a halo lower alkyl group, a cyclic lower alkyl group, an alkenyl group, an alkoxy group, an alkoxy lower alkyl group or an alkylthio group.

$R^{11}$ and $R^{12}$ are the same or different and each independently represents a hydrogen atom, a halogen atom, —$C_hF_{2h+1}$, —$(CH_2)_pR^{20}$, —$(CH_2)_rCOR^{21}$ or —$(CH_2)_t NR^{22}COR^{23}$.

$R^{14}$ and $R^{15}$ are the same or different and each independently represents a hydrogen atom, a halogen atom, a lower alkyl group, a halo lower alkyl group, a cyclic lower alkyl group, an alkenyl group, an alkoxy group, —$C_iF_{2i+1}$, —$(CH_2)_qR^{24}$ or —$(CH_2)_sCOR^{25}$.

In the above definition, $R^{20}$ to $R^{25}$, h, i and p to t are defined below.

$R^{20}$ and $R^{24}$ each independently represents a hydroxyl group or an alkoxy group.

$R^{21}$ and $R^{25}$ each independently represents a hydrogen atom, a hydroxyl group, a lower alkyl group or an alkoxy group.

$R^{22}$ represents a hydrogen atom or a lower alkyl group.

$R^{23}$ represents a hydrogen atom, a lower alkyl group or an alkoxy group.

h and i each independently represents an integer of from 1 to 6.

p and q each independently represents an integer of from 1 to 4.

r and s each independently represents an integer of from 0 to 4.

t represents an integer of from 0 to 4.

More preferably, $R^{10}$ and $R^{13}$ are each independently a lower alkyl group; $R^{11}$ is a chlorine atom; $R^{12}$ is —$(CH_2)_p R^{20}$, (wherein $R^{20}$ is a hydroxyl group, and p is 1) or —$(CH_2)_rCOR^{21}$ (wherein $R^{21}$ is a hydrogen atom, a hydroxyl group or an alkoxy group, and r is 0 or 1); and $R^{14}$ and $R^{15}$ are the same or different and are each independently a hydrogen atom, a lower alkyl group, —$(CH_2)_qR^{24}$ (wherein $R^{24}$ is a hydroxyl group, and q is 1) or —$(CH_2)_s COR^{25}$ (wherein $R^{25}$ is a hydrogen atom, a hydroxyl group or an alkoxy group, and s is 0 or 1).

Definitions for above groups are as hereinbefore set forth. Additionally, the following definitions apply:

The "alkenyl group" is preferably a lower alkenyl group, and more preferably an alkenyl group having not more than 4 carbon atoms. Examples thereof include a vinyl group, an allyl group, a 1-propenyl group and a 1-butenyl group.

The "halo lower alkyl group" is preferably a lower alkyl group substituted with at least one fluorine or chlorine atom, and more preferably —$C_jF_{2j+1}$ (wherein j is from 1 to 6).

The "alkoxy lower alkyl group" is a lower alkyl group having such an alkoxy group, and the alkoxy group is a lower alkoxy group. Examples thereof include a methoxyethyl group, an ethoxymethyl group and a 2-methoxyethyl group.

The "alkylthio group" is preferably a (lower alkyl)thio group. Examples thereof include a methylthio group and an ethylthio group.

Preferred examples of the 2-arylquinolines represented by formula (1) are those wherein $R^1$, $R^3$, $R^4$, $R^5$, $R^6$, $R^7$, $R^8$ and $R^9$ are each independently a hydrogen atom, a halogen atom or a lower alkyl group; $R^2$ is a hydrogen atom, a lower alkyl group or —CH$_2$Q; X is a chlorine atom or a hydrogen atom; and Y is a nitro group or an amino group and positioned at the 2-position of the phenyl group.

More preferred examples of the 2-arylquinolines represented by formula (1) are those wherein $R^1$, $R^3$, $R^4$, $R^5$, $R^6$, $R^7$, $R^8$ and $R^9$ are each a hydrogen atom; $R^2$ is a lower alkyl group or —CH$_2$Q, wherein Q is a 3H-imidazo[4,5-b]pyridin-3-yl group having a substituent(s) or a bromine atom; X is a chlorine atom or a hydrogen atom; and Y is a nitro group or an amino group and positioned at the 2-position of the phenyl group.

Most preferred examples of the 2-arylquinolines represented by formula (1) include 4-chloro-6-methyl-2-(2-nitrophenyl)quinoline, 4-chloro-6-(bromomethyl)-2-(2-nitrophenyl)quinoline, 4-chloro-6-[(2-ethyl-5,7-dimethyl-3H-imidazo[4,5-b]pyridin-3-yl)methyl]-2-(nitrophenyl)quinoline and 2-{6-[(2-ethyl-5,7-dimethyl-3H-imidazo[4,5-b]pyridin-3-yl)methyl]quinolin-2-yl}aniline.

Some of the 2-arylquinolines represented by formula (1) can be produced from the compound represented by formula (2) wherein Y is a nitro group. It is also possible to convert Y of the obtained compound to give other 2-arylquinolines represented by formula (1). In the compounds represented by formula (2), $R^1$ to $R^9$ are preferably the same as $R^1$ to $R^9$ defined in the above description of the 2-arylquinolines represented by formula (1). Similarly, Y is preferably positioned at the 2-position of the phenyl group.

Among the 2-arylquinolines of the present invention represented by formula (1), 4-halo-2-(nitrophenyl) quinolines, wherein X is a halogen atom and Y is a nitro group, can be produced by reacting a 2-(nitrophenyl)-4-quinolone represented by formula (2), wherein Y is a nitro group, with a halogenation agent.

The halogenation agent can be selected from known halogenation agents. Examples thereof include phosphorus oxychloride, phosphorus oxybromide, phosphorus pentachloride and thionyl chloride. The halogenation agent is preferably a chlorination agent, such as phosphorus oxychloride, phosphorus pentachloride and the like, and more preferably phosphorus oxychloride. The halogenation agent is preferably used in an amount of from 1 to 20 equivalents per equivalent of the 2-(nitrophenyl)-4-quinolone. The reaction temperature is preferably from 20° to 130° C.; and the reaction time is appropriately from 0.1 to 10 hours, and preferably from 0.5 to 5 hours.

Subsequently, the product may be separated from the reaction mixture, followed by washing, purification and the like, if necessary. For example, an appropriate solvent (for example, an organic solvent, such as chloroform, methylene chloride and the like) is added to the obtained reaction mixture. After neutralizing with an aqueous alkaline solution, the mixture is evaporated and dried, and the solid matter thus obtained is washed with an appropriate organic solvent (for example, ethyl acetate, toluene, methanol and the like) to obtain an intended product. Alternatively, an appropriate organic solvent (for example, ethyl acetate, toluene and the like) is added to the reaction mixture. After cooling the reaction mixture, the solid matter thus precipitated is taken up by filtration and washed with an appropriate organic solvent (for example, ethyl acetate, toluene, methanol and the like). After distributing into an aqueous basic solution and an appropriate organic solvent (for example, chloroform, methylene chloride and the like), the organic layer is evaporated and dried to obtain an intended 4-halo-2-(2-nitrophenyl)quinoline. The organic layer before evaporating and drying can be used in the next step without evaporating and drying.

The 2-(nitrophenyl)-4-quinolones which are used as the stating material can be synthesized by, for example, a method similar to the method described in K. Bobdanowicz-szwed et al. [Rocz. Chem. Ann. Soc. Chim. Pol., 48:1255 (1974)].

The 2-arylquinolines of the present invention represented by formula (1) wherein X is a hydrogen atom and Y is an amino group, (quinolin-2-yl)anilines, can be produced by reducing the 4-halo-2-(nitrophenyl)quinolines obtained by, for example, the above-mentioned method with a reducing agent in the presence of a base. The base can be selected from known bases. Examples of the base include alkali metal hydroxides (e.g., sodium hydroxide, potassium hydroxide and the like), alkali metal carbonates (e.g., sodium carbonate, potassium carbonate and the like), alkali metal carboxylates (e.g., sodium acetate, potassium acetate and the like) and the like. The base is preferably an alkali metal salt of carboxylic acid having not more than 4 carbon atoms, and more preferably potassium acetate.

The reducing agent can be selected from known reducing agents. It is preferred to perform the reduction by using a hydrogen gas in the presence of a hydrogen reduction catalyst. The hydrogen reduction catalyst can be selected from known hydrogen reduction catalysts. Examples thereof include palladium-carbon catalysts and Raney-nickel catalysts, and palladium/carbon catalysts are preferred. This reduction is usually performed in a solvent. Examples of the solvent include ethanol, methanol, 2-propanol, water, acetic acid, ethyl acetate, toluene, N,N-dimethylformamide, and mixtures of two or more thereof. The reaction temperature is appropriately from 0° C. to the reflux temperature of the solvent.

In the compounds represented by formulae (1) and (2), compounds in which $R^2$ is —CH$_2$Q can be prepared from compounds wherein corresponding $R^2$ is —CH$_3$ according to known methods. For example, compounds wherein $R^2$ is —CH$_2$Q can be prepared by halogenating —CH$_3$ of the corresponding $R^2$ and then reacting it with —QH.

The 2-arylquinolines of the present invention wherein Y is an amino group can be converted into the corresponding trifluoromethanesulfonamides by reacting them with anhydrous trifluoromethanesulfonic acid. This reaction is performed in a solvent, such as methylene chloride, in the presence of a base, such as triethylamine. For example, N-{2-{6-[(2-ethyl-5,7-dimethyl-3H-imidazo[4,5-b]pyridin-3-yl)methyl]quinolin-2-yl}phenyl}trifluoromethanesulfonamide can be 2-{6-[(2-ethyl-5,7-dimethyl-3H-imidazo[4,5-b]pyridin-3-yl)methyl]quinolin-2-yl}aniline at a single step.

The 2-arylquinolines of the present invention are useful as intermediates of angiotensin II antagonists which are useful as a remedy for hypertension. According to the production process of the present invention, these 2-arylquinolines can be easily and efficiently produced.

The present invention is now illustrated in greater detail by way of the following examples, but it should be understood that the present invention is not to be construed as being limited thereto. Unless otherwise indicated, all parts, percents, ratios and the like are by weight.

REFERENCE EXAMPLE 1

Synthesis of N-(4'-methylphenyl)-3-(4'-methylanilino)-3-(2-nitrophenyl)acrylamide To a suspension of 125 ml of ethanol containing 70.5 g (615 mmol) of magnesium ethylate, 250 ml of toluene containing 96.0 g (600 mmol) of diethyl malonate was added dropwise. After stirring at a bath temperature of 70° C. for 2 hours, the thus-prepared reaction mixture was cooled to 0° C., and 62.5 ml of toluene containing 105 g (565 mmol) of 2-nitrobenzoyl chloride was added dropwise thereto. After stirring at room temperature for 3 hours, 250 ml of water containing 60 g of sulfuric acid was added thereto, and the thus-prepared mixture was poured into 350 ml of water and separated out. The organic layer obtained was washed with 350 ml of a saturated aqueous solution of sodium chloride and dried over magnesium sulfate. After filtration and concentration, the resulting residue was dried in vacuo to obtain 187.5 g of a crude product of diethyl 2-(2-nitrobenzoyl)malonate.

To 187.5 g of this crude product, 250 ml of water and 262 mg (1.375 mmol) of p-toluenesulfonic acid monohydrate were added. The thus-prepared mixture was heated under reflux for 2.5 hours and then cooled to room temperature. After adding 250 ml of chloroform thereto, the thus-prepared mixture was separated out. The organic layer obtained was washed with 250 ml of a 7% aqueous solution of sodium bicarbonate and 250 ml of a saturated aqueous solution of sodium chloride. After drying over magnesium sulfate, the resulting residue was filtered, concentrated and dried in vacuo to prepare 138.5 g of a crude product of ethyl 2-nitrobenzoylacetate. To this crude product, 377 ml of toluene, 121 g (1.13 mol) of p-toluidine and 1.6 g (11.3 mmol) of p-toluidine hydrochloride were added, and the thus-prepared mixture was heated under reflux for 8.5 hours using a Dean-Stark trap. During this reflux, about 39 ml of water containing ethanol was distilled off. After further distilling off 283 ml of toluene, the mixture was cooled to 0° C., and 100 ml of a 5% aqueous solution of potassium hydroxide dissolved in ethanol/water (9/1) was added thereto. The thus-prepared mixture was stirred at room temperature for 10 minutes, and the crystals precipitated were collected by filtration.

Next, the resulting filtration residue was washed successively with 50 ml of a 5% potassium hydroxide solution dissolved in ethanol/water (9/1) twice and 50 ml of ethanol/water (9/1) twice and then dried in vacuo to obtain 145.5 g of N-(4'-methylphenyl)-3-(4'-methylanilino)-3-(2-nitrophenyl)acrylamide.

NMR (400 MHz, CDCl$_3$): δ11.14 (s, 1H); 6.63–7.88 (m, 13H); 4.66 (s, 1H); 2.31 (s, 3H); 2.19 (s, 3H)

REFERENCE EXAMPLE 2

Synthesis of 6-methyl-2-(2-nitrophenyl)-4-quinolone:

To 727.5 g of polyphosphoric acid, 145.5 g of N-(4'-methylphenyl)-3-(4'-methylanilino)-3-(2-nitrophenyl)acrylamide obtained in Reference Example 1 was added, and the thus-prepared mixture was stirred at from 100° to 115° C. for 5 hours and then poured into 1,455 g of ice water. After allowing to stand overnight, the solid precipitated was collected by decantation. After adding water thereto, this solid was broken in water and filtered. The resulting filtration residue was washed with 500 ml of water twice and dried under reduced pressure at 60° C. Then, 500 ml of methanol was added to the solid which was then suspended therein. After stirring for 2 hours, the solid was collected by filtration, washed with 250 ml of methanol twice and dried under reduced pressure at 40° C. to obtain 53.3 g of 6-methyl-2-(2-nitrophenyl)-4-quinolone. Furthermore, 17.4 g of the product was obtained from the filtrate.

NMR (400 MHz, DMSO-d$_6$): δ8.20–8.28 (m, 1H); 7.75–7.95 (m, 4H); 7.41–7.56 (m, 2H); 6.00 (bs, 1H); 2.43 (s, 3H)

EXAMPLE 1

Synthesis of 4-chloro-6-methyl-2-(2-nitrophenyl)quinoline

To 63.9 ml of phosphorus oxychloride, 53.3 g of 6-methyl-2-(2-nitrophenyl)-4-quinolone obtained in Reference Example 2 was added, and the thus-prepared mixture was heated to 110° C. and stirred for 4 hours. Then, the mixture was poured into 640 g of ice water, and 1,600 ml of chloroform was added thereto under stirring, followed by neutralization with a 10N aqueous solution of sodium hydroxide. The resulting organic layer was washed with 640 ml of water, and evaporated and dried in an evaporator to obtain 55.0 g of a crude product of 4-chloro-6-methyl-2-(2-nitrophenyl)quinoline. A 38.06 g portion of this crude product was taken, and 380 ml of methanol was added thereto. Then, the thus-prepared mixture was suspended for a while and filtered. The resulting filtrate was washed with 190 ml of methanol twice and dried under reduced pressure to obtain 29.5 g of 4-chloro-6-methyl-2-(2-nitrophenyl)quinoline. Furthermore, 5.00 g of the crude product was recrystallized from ethyl acetate to obtain 3.26 g of the intended compound.

NMR (400 MHz, CDCl$_3$): δ7.98–8.03 (m, 3H); 7.58–7.72 (m, 5H); 2.61 (s, 3H)

EXAMPLE 2

Synthesis of 4-chloro-6-(bromomethyl)-2-(2-nitrophenyl)quinoline (No. 1)

To 27.6 g (92.4 mmol) of the 4-chloro-6-methyl-2-(2-nitrophenyl)quinoline obtained in Example 1, 110 ml of chloroform was added. After stirring, 15.6 g (87.8 mmol) of N-bromosuccinimide (NBS) was added thereto. Then, 15 ml of chloroform containing 0.78 g of 2,2'-azobis(2,4-dimethylvaleronitrile) was added dropwise thereto, and the thus-prepared mixture was heated under reflux for 1 hour. After cooling to room temperature, the mixture was poured into 220 ml of water and separated out, and the organic layer was washed with 110 ml of water twice. Next, the washed organic layer was evaporated and dried in an evaporator and recrystallized from toluene to obtain 14.7 g of 4-chloro-6-(bromomethyl)-2-(2-nitrophenyl)quinoline.

NMR (400 MHz, CDCl$_3$): δ8.25 (s, 1H); 8.09 (d, J=8.8 Hz, 1H); 8.02 (d, J=8.0 Hz, 1H); 7.60–7.84 (m, 5H); 4.71 (s, 2H)

EXAMPLE 3

Synthesis of 4-chloro-6-(bromomethyl)-2-(2-nitrophenyl)quinoline (No. 2)

To 21 ml of phosphorus oxychloride, 21.0 g of 6-methyl-2-(2-nitrophenyl)-4-quinolone obtained in Reference Example 2 was added and stirred at 110° C. for 2 hours. After cooling to room temperature, 21 ml of ethyl acetate was added thereto, stirred for a while and filtrated. The resulting filtration residue was washed with 20 ml of ethyl acetate twice, and the resulting solid was poured into a mixture of a saturated aqueous solution of sodium bicarbonate (100 ml) with chloroform (100 ml) under stirring. After separating out, the resulting organic layer was dried over magnesium sulfate and filtered. To the resulting filtrate, 13.3 g (74.9 mmol) of NBS was added under stirring. Then, 13 ml of chloroform containing 0.665 g of 2,2'-azobis(2,4-dimethylvaleronitrile) was added dropwise thereto, and the thus-obtained mixture was heated under reflux for 2.5 hours. After cooling to room temperature, the mixture was poured into 210 ml of water and separated out. The resulting organic layer was washed with 210 ml of water twice, evaporated and dried in an evaporator and recrystallized from toluene to obtain 9.16 g of 4-chloro-6-(bromomethyl)-2-(2-nitrophenyl)quinoline.

EXAMPLE 4

Synthesis of 4-chloro-6-[(2-ethyl-5,7-dimethyl-3H-imidazo[4,5-b]pyridin-3-yl)methyl]-2-(nitrophenyl)quinoline To 61 ml of N,N-dimethylformamide (DMF) containing 7.45 g (42.5 mmol) of 2-ethyl-5,7-dimethyl-1H-imidazo[4,5-b]pyridine, 1.79 g (44.6 mmol) of sodium hydride (60%) was added and stirred at room temperature for 30 minutes. To the thus-prepared mixture, 15.3 g of 4-chloro-6-(bromomethyl)-2-(2-nitrophenyl)quinoline was added and stirred at room temperature for 12 hours. After adding 120 ml of toluene thereto, the thus-prepared mixture was poured into a mixture of 60 ml of toluene with 300 ml of water. After adding 120 ml of ethyl acetate thereto, the mixture was separated out and the resulting aqueous layer was extracted with a mixture of 90 ml of toluene with 90 ml of ethyl acetate. The resulting organic layers were combined and evaporated to 117.82 g in an evaporator. Then, 90 ml of toluene was added thereto and the thus-prepared mixture was washed with 90 ml of water twice. The resulting insolubles were filtered off and the organic layer was concentrated to 58.3 g in an evaporator. After allowing to stand at 5° C., the crystals precipitated were collected, washed with 10 ml of toluene twice and dried to obtain 8.12 g of 4-chloro-6-[(2-ethyl-5,7-dimethyl-3H-imidazo[4,5-b]pyridin-3-yl)methyl]-2-(nitrophenyl)quinoline.

NMR (400 MHz, CDCl$_3$): δ8.08 (s, 1H); 8.01 (d, J=8.0 Hz, 2H); 7.53–7.72 (m, 5H); 6.93 (s, 1H); 5.69 (s, 2H); 2.84 (q, J=7.6 Hz, 2H); 2.66 (s, 3H); 2.61 (s, 3H); 1.36 (t, J=7.6 Hz, 3H).

EXAMPLE 5

Synthesis of 2-{6-[(2-ethyl-5,7-dimethyl-3H-imidazo[4,5-b]pyridin-3-yl)methyl]quinolin-2-yl}aniline (No. 1)

To 240 ml of methanol containing 8.0 g of potassium hydroxide, 8.12 g (17.2 mmol) of 4-chloro-6-[(2-ethyl-5,7-dimethyl-3H-imidazo[4,5-b]pyridin-3-yl)methyl]-2-(nitrophenyl)quinoline obtained in Example 4 and 0.80 g of a 5% palladium-carbon catalyst were added and the thus-prepared mixture was stirred under a hydrogen atmosphere for 17 hours. After adding 120 ml of chloroform thereto, the thus-prepared mixture was filtered through celite. To the resulting filtrate, 120 ml of water was added, and the thus-prepared mixture was then separated out. The resulting organic layer was washed with 120 ml of water. Then, 60 ml of water was added to the organic layer, and a 130 ml portion thereof was distilled off by heating under atmospheric pressure. After allowing to stand at 0° C., the crystals precipitated were collected by filtration, and the resulting filtration residue was further recrystallized from a mixture of chloroform with methanol to obtain 3.30 g of 2-{6-[(2-ethyl-5,7-dimethyl-3H-imidazo[4,5-b]pyridin-3-yl)methyl]quinolin-2-yl}aniline.

NMR (400 MHz, CDCl$_3$): δ8.06 (d, J=8.8 Hz, 1H); 7.97 (d, J=8.8 Hz, 1H); 7.80 (d, J=8.8 Hz, 1H); 7.66 (d, J=7.6 Hz, 1H); 7.51 (dd, J=2, 8.8 Hz, 1H); 7.41 (s, 1H); 7.20 (dd, J=7.0, 1.2 Hz, 1H); 6.93 (s, 1H); 6.80 (t, J=8.0 Hz, 2H); 6.15 (bs, 2H); 5.64 (s, 2H); 2.81 (q, J=7.6 Hz, 2H); 2.67 (s, 3H); 2.61 (s, 3H); 1.31 (t, J=7.6 Hz, 3H)

EXAMPLE 6

Synthesis of 2-{6-[(2-ethyl-5,7-dimethyl-3H-imidazo[4,5-b]pyridin-3-yl)methyl]quinolin-2-yl}aniline (No. 2)

To 2.04 g of a 5% palladium-carbon catalyst, 15 ml of water containing 10.2 g of potassium acetate was added. Then, a solution of 10.18 g (21.6 mmol) of 4-chloro-6-[(2-ethyl-5,7-dimethyl-3H-imidazo[4,5-b]pyridin-3-yl)methyl]-2-(nitrophenyl)quinoline obtained in Example 4 dissolved in 30 ml of ethyl acetate and 240 ml of ethanol at 70° C. was added thereto, and the thus-prepared mixture was stirred under a hydrogen atmosphere at 60° C. for 3 hours. After adding 150 ml of chloroform and 200 ml of water thereto, the thus-prepared mixture was filtered through celite. The resulting filtrate was separated out, and the organic layer obtained was concentrated to 95.0 g in an evaporator. After allowing to stand at 0° C., the crystals precipitated were collected by filtration. The resulting filtration residue was washed with 10 ml of ethanol three times and dried under reduced pressure at 40° C. to obtain 6.70 g of 2-{6-[(2-ethyl-5,7-dimethyl-3H-imidazo[4,5-b]pyridin-3-yl)methyl]quinolin-2-yl}aniline.

The 2-arylquinolines of the present invention are useful as intermediates of angiotensin II antagonists which are useful as a remedy for hypertension. According to the production process of the present invention, these 2-arylquinolines can be easily and efficiently produced.

While the invention has been described in detail and with reference to specific embodiments thereof, it will be apparent to one skilled in the art that various changes and modifications can be made therein without departing from the spirit and scope thereof.

This application is based on application No. Hei 8-11257 filed in Japan, the content of which is incorporated to by reference.

What is claimed is:

1. 2-Arylquinoline represented by the following formula (1):

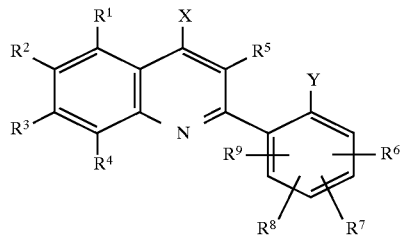

wherein $R^1$, $R^3$, $R^4$, $R^5$, $R^6$, $R^7$, $R^8$ and $R^9$ each independently represents a hydrogen atom, a halogen atom, a lower alkyl group, a cyclic lower alkyl group, an aryl group, an aralkyl group, an alkoxy group or —$C_mF_{2m+1}$;

$R^2$ represents a hydrogen atom, a halogen atom, a lower alkyl group, a cyclic lower alkyl group, an aryl group, an aralkyl group, an alkoxy group, —$C_nF_{2n+1}$ or —$CH_2Q$, in which Q represents a monovalent organic group obtained by eliminating from an organic compound having an —NH— group the hydrogen atom bonded to the nitrogen atom or Q represents a halogen atom;

X represents a halogen atom;

Y represents a nitro group, an amino group or an amino group protected with a protecting group; and m and n each independently represents an integer of from 1 to 6.

2. The compound as claimed in claim 1, wherein $R^1$, $R^3$, $R^4$, $R^5$, $R^6$, $R^7$, $R^8$ and $R^9$ are each independently a hydrogen atom, a halogen atom or a lower alkyl group; and $R^2$ is a hydrogen atom, a lower alkyl group or —$CH_2Q$.

3. 2-Arylquinoline represented by the following formula (1):

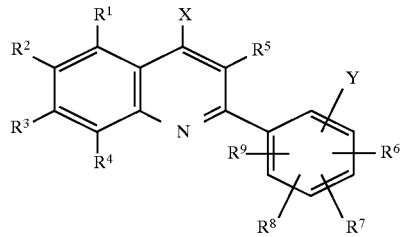

wherein $R^1$, $R^3$, $R^4$, $R^5$, $R^6$, $R^7$, $R^8$ and $R^9$ each independently represents a hydrogen atom, a halogen atom, a lower alkyl group, a cyclic lower alkyl group, an aryl group, an aralkyl group, an alkoxy group or —$C_mF_{2m+1}$;

$R^2$ represents —$CH_2Q$, in which Q represents a monovalent organic group obtained by eliminating from an organic compound having an —NH— group the hydrogen atom bonded to the nitrogen atom or Q represents a halogen atom;

X represents a hydrogen atom;

Y represents a nitro group, an amino group or an amino group protected with a protecting group; and m represents an integer of from 1 to 6.

4. 2-Arylquinoline represented by the following formula (1):

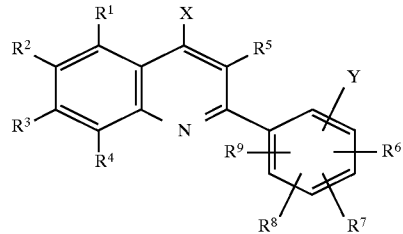

wherein $R^1$, $R^3$, $R^4$, $R^5$, $R^6$, $R^7$, $R^8$ and $R^9$ each independently represents a hydrogen atom, a halogen atom, a lower alkyl group, a cyclic lower alkyl group, a aryl group, an aralkyl group, an alkoxy group or —$C_mF_{2m+1}$;

$R^2$ represents —$CH_2Q$, in which Q represents a 3H-imidazo[4,5-b]pyridin-3-yl group which is optionally substituted or Q represents a bromine atom;

X represents a halogen atom or a hydrogen atom;

Y represents a nitro group, an amino group or an amino group protected with a protecting group; and m represents an integer of from 1 to 6.

5. The compound as claimed in claim 1, 2 or 3, wherein Q is a 3H-imidazo[4,5-b]pyridin-3-yl group having a substituent(s) or a bromine atom.

6. The compound as claimed in claim 1, wherein X is a chlorine atom; and Y is a nitro group or an amino group.

7. The compound as claimed in claim 1, wherein $R^1$, $R^3$, $R^4$, $R^5$, $R^6$, $R^7$, $R^8$ and $R^9$ are each a hydrogen atom; $R^2$ is a lower alkyl group or —$CH_2Q$, in which Q is a 3H-imidazo[4,5-b]pyridin-3-yl group having a substituent(s) or a bromine atom; X is a chlorine atom; and Y is a nitro group or an amino group.

8. 4-chloro-6-[(2-ethyl-5,7-dimethyl-3H-imidazo[4,5-b]pyridin-3-yl)methyl]-2-(2-nitrophenyl)quinoline or 2-{6-[(2-ethyl-5,7-dimethyl-3H-imidazo[4,5-b]pyridin-3-yl)methyl]quinolin-2-yl}aniline.

9. A process for producing a 4-halo-2-(nitrophenyl) quinoline represented by the following formula (1), wherein X represents a halogen atom, and Y represents a nitro group, which comprises reacting a 2-(nitrophenyl)-4-quinolone represented by the following formula (2), wherein Y represents a nitro group, with a halogenation agent:

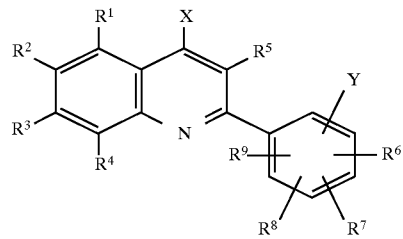

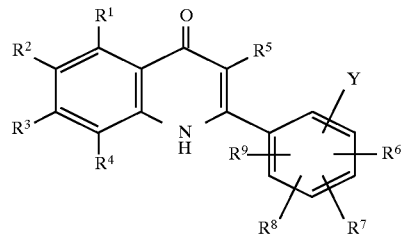

wherein, in formulae (1) and (2), $R^1$, $R^3$, $R^4$, $R^5$, $R^6$, $R^7$, $R^8$ and $R^9$ each independently represents a hydrogen atom, a halogen atom, a lower alkyl group, a cyclic lower alkyl group, an aryl group, an aralkyl group, an alkoxy group or —$C_mF_{2m+1}$;

$R^2$ represents a hydrogen atom, a halogen atom, a lower alkyl group, a cyclic lower alkyl group, an aryl group, an aralkyl group, an alkoxy group, —$C_nF_{2n+1}$ or —$CH_2Q$, in which Q represents a monovalent organic group obtained by eliminating from an organic compound having an —NH— group the hydrogen atom bonded to the nitrogen atom, or a halogen atom; and m and n each independently represents an integer of from 1 to 6.

10. The process as claimed in claim 9, wherein $R^1$, $R^3$, $R^4$, $R^5$, $R^6$, $R^7$, $R^8$ and $R^9$ are each independently a hydrogen atom, a halogen atom or a lower alkyl group; $R^2$ is a hydrogen atom, a lower alkyl group or —$CH_2Q$; and Y is positioned at the 2-position of the phenyl group.

11. The process as claimed in claim 9 or 10, wherein Q is a 3H-imidazo[4,5-b]pyridin-3-yl group having a substituent (s) or a bromine atom.

12. The process as claimed in claim 9, wherein X is a chlorine atom.

13. The process as claimed in claim 9, wherein $R^1$, $R^3$, $R^4$, $R^5$, $R^6$, $R^7$, $R^8$ and $R^9$ are each a hydrogen atom; $R^2$ is a lower alkyl group or —$CH_2Q$, in which Q is a 3H-imidazo [4,5-b]pyridin-3-yl group having a substituent(s) or a bromine atom; X is a chlorine atom; and Y is positioned at the 2-position of the phenyl group.

14. The process as claimed in claim 9, wherein the 2-(nitrophenyl)-4-quinolone represented by formula (2) is 6-methyl-2-(2-nitrophenyl)-4-quinolone; and the 4-halo-2-(nitrophenyl)quinoline represented by formula (1) is 4-chloro-6-methyl-2-(2-nitrophenyl)quinoline.

15. The process as claimed in claim 9, wherein the halogenation agent is a chlorination agent.

16. A process for producing a (quinolin-2-yl)aniline represented by the following formula (1), wherein X represents a hydrogen atom, and Y represents an amino group, which comprises reducing 4-halo-2-(nitrophenyl) quinoline represented by formula (1), wherein X represents a halogen atom, and Y represents a nitro group, with a reducing agent in the presence of a base

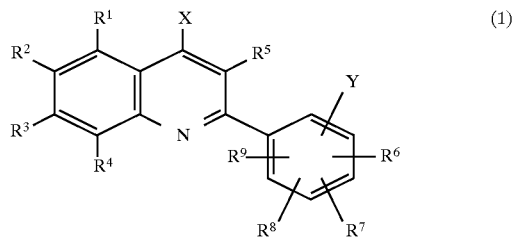

wherein $R^1$, $R^3$, $R^4$, $R^5$, $R^6$, $R^7$, $R^8$ and $R^9$ each independently represents a hydrogen atom, a halogen atom, a lower alkyl group, a cyclic lower alkyl group, an aryl group, an aralkyl group, an alkoxy group or —$C_mF_{2m+1}$;

$R^2$ represents a hydrogen atom, a halogen atom, a lower alkyl group, a cyclic lower alkyl group, an aryl group, an aralkyl group, an alkoxy group, —$C_nF_{2n+1}$ or —$CH_2Q$, in which Q represents a monovalent organic group obtained by eliminating from an organic compound having an —NH— group the hydrogen atom bonded to the nitrogen atom or Q represents a halogen atom; and m and n each independently represents an integer of from 1 to 6.

17. The process as claimed in claim 16, wherein $R^1$, $R^3$, $R^4$, $R^5$, $R^6$, $R^7$, $R^8$ and $R^9$ are each independently a hydrogen atom, a halogen atom or a lower alkyl group; $R^2$ is a hydrogen atom, a lower alkyl group or —$CH_2Q$; and Y is positioned at the 2-position of the phenyl group.

18. The process as claimed in claim 16 or 17, wherein Q is a 3H-imidazo[4,5-b]pyridin-3-yl group having a substituent(s).

19. The process as claimed in claim 16, wherein the halogen atom represented by X is a chlorine atom.

20. The process as claimed in claim 16, wherein $R^1$, $R^3$, $R^4$, $R^5$, $R^6$, $R^7$, $R^8$ and $R^9$ are each a hydrogen atom; $R^2$ is a lower alkyl group or —$CH_2Q$, in which Q is a 3H-imidazo [4,5-b]pyridin-3-yl group having a substituent(s); X is a chlorine atom; and Y is positioned at the 2-position of the phenyl group.

21. The process as claimed in claim 16, wherein the 4-halo-2-(nitrophenyl)quinoline represented by formula (1) is 4-chloro-6-[(2-ethyl-5,7-dimethyl-3H-imidazo[4,5-b] pyridin-3-yl)methyl]-2-(2-nitrophenyl)quinoline and the (quinolin-2-yl)aniline represented by formula (1) is 2-{6-[ (2-ethyl-5,7-dimethyl-3H-imidazo[4,5-b]pyridin-3-yl) methyl]quinolin-2-yl}aniline.

22. The process as claimed in claim 16, wherein the reducing agent is hydrogen which is used in the presence of a hydrogen reduction catalyst; and the base is an alkali metal salt of carboxylic acid.

23. The compound as claimed in claim 4, wherein Q is 3H-imidazo[4,5b]pyridin-3-yl group having at least one substituent.

24. The compound as claimed in claim 4, wherein Q is a bromine atom.

25. The compound as claimed in claim 8, which is 4chloro-6-[(2-ethyl-5,7-dimethyl-3H-imidazo[4,5-b] pyridin-3-yl)methyl]-2-(2-nitrophenyl)quinoline.

26. The compound as claimed in claim 8, which is 2-{6-[(2-ethyl-5,7-dimethyl-3H-imidazo[4,5-b]pyridin-3-yl)methyl]quinolin-2-yl}aniline.

27. The compound as claimed in claim 3, wherein $R^1$, $R^3$, $R^4$, $R^5$, $R^6$, $R^7$, $R^8$ and $R^9$ are each independently a hydrogen atom, a halogen atom or a lower alkyl group.

28. The compound as claimed in claim 3, wherein X is a hydrogen atom; and Y is a nitro group or an amino group and positioned at the 2-position of the phenyl group.

29. The compound as claimed in claim 3, wherein $R^1$, $R^3$, $R^4$, $R^5$, $R^6$, $R^7$, $R^8$ and $R^9$ are each a hydrogen atom; $R^2$ is —$CH_2Q$, in which Q is a 3H-imidazo[4,5-b]pyridin-3-yl group having a substituent(s) or a bromine atom; and Y is a nitro group or an amino group and positioned at the 2-position of the phenyl group.

* * * * *